(12) United States Patent
Montgomery, II et al.

(10) Patent No.: US 12,721,532 B2
(45) Date of Patent: Sep. 1, 2026

(54) NON-INVASIVE BLOOD PRESSURE MEASUREMENT TECHNIQUES BASED ON WAVE SHAPE CHANGE DURING AN EXTERNAL PRESSURE CYCLE

(71) Applicant: Apple Inc., Cupertino, CA (US)

(72) Inventors: Robert K. Montgomery, II, Cupertino, CA (US); Chin San Han, Mountain View, CA (US)

(73) Assignee: Apple Inc., Cupertino, CA (US)

( * ) Notice: Subject to any disclaimer, the term of this patent is extended or adjusted under 35 U.S.C. 154(b) by 1385 days.

(21) Appl. No.: 17/354,775

(22) Filed: Jun. 22, 2021

(65) Prior Publication Data

US 2022/0400959 A1 Dec. 22, 2022

(51) Int. Cl.
*A61B 5/022* (2006.01)
*A61B 3/16* (2006.01)
*A61B 5/021* (2006.01)

(52) U.S. Cl.
CPC ................ *A61B 5/022* (2013.01); *A61B 3/16* (2013.01); *A61B 5/02108* (2013.01)

(58) Field of Classification Search
CPC ....... A61B 5/022; A61B 3/16; A61B 5/02108; A61B 5/02141; A61B 5/02225; A61B 5/02255
See application file for complete search history.

(56) References Cited

U.S. PATENT DOCUMENTS

| | | | |
|---|---|---|---|
| 4,005,701 | A | 2/1977 | Aisenberg et al. |
| 4,290,434 | A | 9/1981 | Jewett |
| 4,548,198 | A | 10/1985 | Manes |

(Continued)

FOREIGN PATENT DOCUMENTS

| | | |
|---|---|---|
| CN | 103598879 | 2/2014 |
| CN | 104545892 | 4/2015 |

(Continued)

OTHER PUBLICATIONS

Horsey, "YHE smartwatch wearable blood pressure monitor," geeky-gadgets.com/wearable-blood-pressure-monitor-07-02-2020, Feb. 7, 2020, 3 pages.

(Continued)

*Primary Examiner* — Justin Xu
(74) *Attorney, Agent, or Firm* — Brownstein Hyatt Farber Schreck, LLP

(57) ABSTRACT

Embodiments include systems and methods for determining blood pressure of a user. Embodiments can include a restriction device that is configured to apply an external pressure cycle to a blood vessel of the user and a pressure sensing device that is configured to detect pressures within the blood vessel during the external pressure cycle and output a signal indicative of the detected pressures. Embodiments can also include a processing device that is configured to receive the signal from the pressure sensing device, determine a first set of pressure values corresponding to minimum pressure values for each pulse pressure wave and determine a second set of pressure values corresponding to pressure upstrokes that occur during a descending pressure phase of a respective pulse pressure wave. The system can determine a blood pressure parameter of the user based on the first set of pressure values and the second set of pressure values.

19 Claims, 9 Drawing Sheets

(56) References Cited

U.S. PATENT DOCUMENTS 4,896,676 A 1/1990 Sasaki
5,135,003 A 8/1992 Souma
5,632,278 A 5/1997 Rometsch
5,666,404 A 9/1997 Ciccotelli et al.
6,162,181 A 12/2000 Hynson et al.
6,497,668 B2 12/2002 Nishibayashi
6,689,069 B2 2/2004 Bratteli et al.
6,694,821 B2 2/2004 Yamakoshi et al.
6,705,998 B2 3/2004 Stergiopoulos et al.
6,814,077 B1 11/2004 Eistert
7,111,625 B2 9/2006 Jackson
7,678,059 B2 3/2010 Friedman et al.
7,927,283 B2 4/2011 Riobo Aboy
8,690,799 B2 4/2014 Telfort et al.
8,911,378 B2 12/2014 Whitaker et al.
8,998,817 B2 4/2015 Pfeiffer et al.
9,192,351 B1 11/2015 Telfort et al.
9,198,584 B2 12/2015 Yamashita et al.
9,986,919 B2 6/2018 Lamego et al.
10,064,561 B2 9/2018 Kinoshita et al.
10,405,806 B2 9/2019 Baik et al.
10,502,328 B2 12/2019 Kotani et al.
10,874,307 B2 12/2020 Narasimhan et al.
11,134,901 B2 10/2021 Fine et al.
11,172,839 B2 11/2021 Ward et al.
11,179,049 B2 11/2021 Niehaus et al.
11,298,032 B2 4/2022 Mou et al.
11,576,583 B2 2/2023 Dana et al.
2004/0044288 A1 3/2004 Gorenberg et al.
2006/0111637 A1 5/2006 Jacober et al.
2007/0185402 A1 8/2007 Yang et al.
2007/0203416 A1 8/2007 Lowe
2009/0012411 A1 1/2009 Lowe et al.
2010/0106029 A1 4/2010 Fraden
2012/0136262 A1 5/2012 Sawanoi et al.
2012/0209129 A1 8/2012 Smith et al.
2012/0277602 A1* 11/2012 Tichauer .............. A61B 5/0225 600/494
2013/0060147 A1 3/2013 Welch et al.
2013/0144176 A1 6/2013 Lec
2013/0150736 A1* 6/2013 Romano ............ A61B 5/02108 600/485
2014/0187987 A1 7/2014 Fraden et al.
2014/0309541 A1 10/2014 Yamashita et al.
2015/0105675 A1 4/2015 Nakagawa et al.
2016/0038044 A1 2/2016 Banerjee et al.
2016/0106326 A1 4/2016 Bajaj et al.
2016/0120418 A1 5/2016 Oksala et al.
2017/0273579 A1 9/2017 Mori et al.
2017/0290519 A1 10/2017 Zhou
2018/0177411 A1 6/2018 Du et al.
2018/0184920 A1 7/2018 Rabinovich et al.
2018/0338693 A1 11/2018 Li et al.
2019/0261870 A1 8/2019 Nishikawa
2020/0323446 A1 10/2020 Nishida et al.
2021/0030372 A1* 2/2021 Lizio .................. A61B 5/02405
2021/0059537 A1 3/2021 Nakagawa et al.
2021/0127993 A1 5/2021 Matsumura et al.
2021/0169347 A1 6/2021 Ito et al.
2021/0236012 A1 8/2021 Nishida et al.
2021/0251499 A1 8/2021 Ogawa
2021/0285436 A1 9/2021 Fukami et al.
2021/0321889 A1 10/2021 Jain et al.
2022/0000380 A1 1/2022 Li et al.
2022/0015652 A1 1/2022 Lee et al.
2022/0054020 A1 2/2022 Tadele et al.
2022/0087545 A1 3/2022 Jain et al.
2022/0240803 A1 8/2022 Han et al.
2022/0400959 A1 12/2022 Montgomery et al.
2023/0063813 A1 3/2023 Smith et al.
2023/0068620 A1 3/2023 Tadele et al.

FOREIGN PATENT DOCUMENTS

CN 106037698 10/2016
CN 110099607 8/2019
CN 110301906 10/2019
GB 2575945 1/2020
JP 3120617 U 3/2006
JP 3121082 U 4/2006
JP 2008178541 8/2008
JP 2020043931 3/2020
JP 2021143647 9/2021
KR 20180033018 4/2018
WO WO 11/023343 3/2011
WO WO 20/016139 1/2020

OTHER PUBLICATIONS

U.S. Appl. No. 18/593,644, filed Mar. 1, 2024, Han.
U.S. Appl. No. 16/928,933, filed Jul. 14, 2020, Lee et al.
U.S. Appl. No. 16/998,902, filed Aug. 20, 2020, Tadele et al.
U.S. Appl. No. 17/166,914, filed Feb. 3, 2021, Han et al.
U.S. Appl. No. 17/398,775, filed Aug. 10, 2021, Jain et al.
U.S. Appl. No. 17/899,443, filed Aug. 30, 2022, Smith et al.
U.S. Appl. No. 17/900,678, filed Aug. 31, 2022, Tadele et al.

* cited by examiner

NON-INVASIVE BLOOD PRESSURE MEASUREMENT TECHNIQUES BASED ON WAVE SHAPE CHANGE DURING AN EXTERNAL PRESSURE CYCLE

FIELD

The described embodiments relate generally to systems and techniques for determining physical parameters of a user. More particularly, the present embodiments relate to systems and methods for obtaining and analyzing non-invasive blood pressure measurement data.

BACKGROUND

Various non-invasive blood pressure measurement techniques are commonly used to determine the blood pressure of a user. Auscultation and oscillometry are popular methods of non-invasively measuring blood pressure of a user due to their ease of use and ability to be performed in remote settings such as a user's home. However, non-invasive blood pressure measurement methods, such as these, tend to have lower accuracy and/or greater variability as compared to invasive measurement techniques such as direct intra-arterial sensing.

SUMMARY

Embodiments are directed to a system for determining blood pressure of a user. The system can include a restriction device configured to apply an external pressure cycle to a blood vessel of the user and a pressure sensing device configured to detect pressures within the blood vessel during the external pressure cycle and output a signal indicative of the detected pressures. The system can also include a processing device configured to receive the signal from the pressure sensing device and determine a set of pressure measurements for a set of pulse pressure waves within the blood vessel during the external pressure cycle based on the signal. The processing device can be further configured to determine a first set of pressure values, where each pressure value in the first set of pressure values corresponds to a minimum pressure value for a respective pulse pressure wave in the set of pulse pressure waves, and to determine a second set of pressure values, where each second pressure value in the second set of pressure values corresponds to a pressure upstroke that occurs during a descending pressure phase of the respective pulse pressure wave in the set of pulse pressure waves. The processing device can determine a blood pressure parameter of the user based on the first set of pressure values and the second set of pressure values.

Embodiments also include methods for determining a blood pressure parameter of a user. The methods can include causing a restriction device to apply an external pressure cycle to a blood vessel of the user and receiving a set of pressure signals corresponding to a set of measured pulse pressure waves occurring within the blood vessel during the external pressure cycle. The methods can include determining a first set of pressure values from the set of pressure signals, where each pressure value in the first set of pressure values corresponds to a minimum pressure for a respective pulse pressure wave in the set of measured pulse pressure waves and generating a first fit parameter based on the first set of pressure values. The methods can further include determining a second set of pressure values, where each second pressure value in the second set of pressure values corresponds to a pressure upstroke that occurs during a descending pressure phase of the respective pulse pressure wave in the set of measured pulse pressure waves, and generating a second fit parameter based on the second set of pressure values. The methods can include determining an intersection point of the first fit parameter and the second fit parameter, using the intersection point to identify a corresponding pressure wave in the set of measured pulse pressure waves, and determining the blood pressure parameter of the user using the corresponding pressure wave.

Embodiments are also directed to a blood pressure measurement device that includes a restriction device configured to wrap around a limb of a user and apply an external pressure cycle to a blood vessel of the user and a pressure sensing device coupled to the restriction device. The pressure sensing device can be configured to detect pressures within the blood vessel during the external pressure cycle and output a signal indicative of the detected pressures. The device can include a processing device configured to receive the signal from the pressure sensing device, and analyze the signal to determine, for each pulse pressure wave occurring in the blood vessel during the external pressure cycle, a local minimum pressure value that occurs between subsequent pulse pressure waves and a descending pressure value that occurs during a descending phase of each pulse pressure wave. The device can determine a blood pressure parameter of the user based on the local minimum pressure value and the descending pressure value for each pulse pressure wave.

BRIEF DESCRIPTION OF THE DRAWINGS

The disclosure will be readily understood by the following detailed description in conjunction with the accompanying drawings, wherein like reference numerals designate like structural elements, and in which.

Figure 1A:
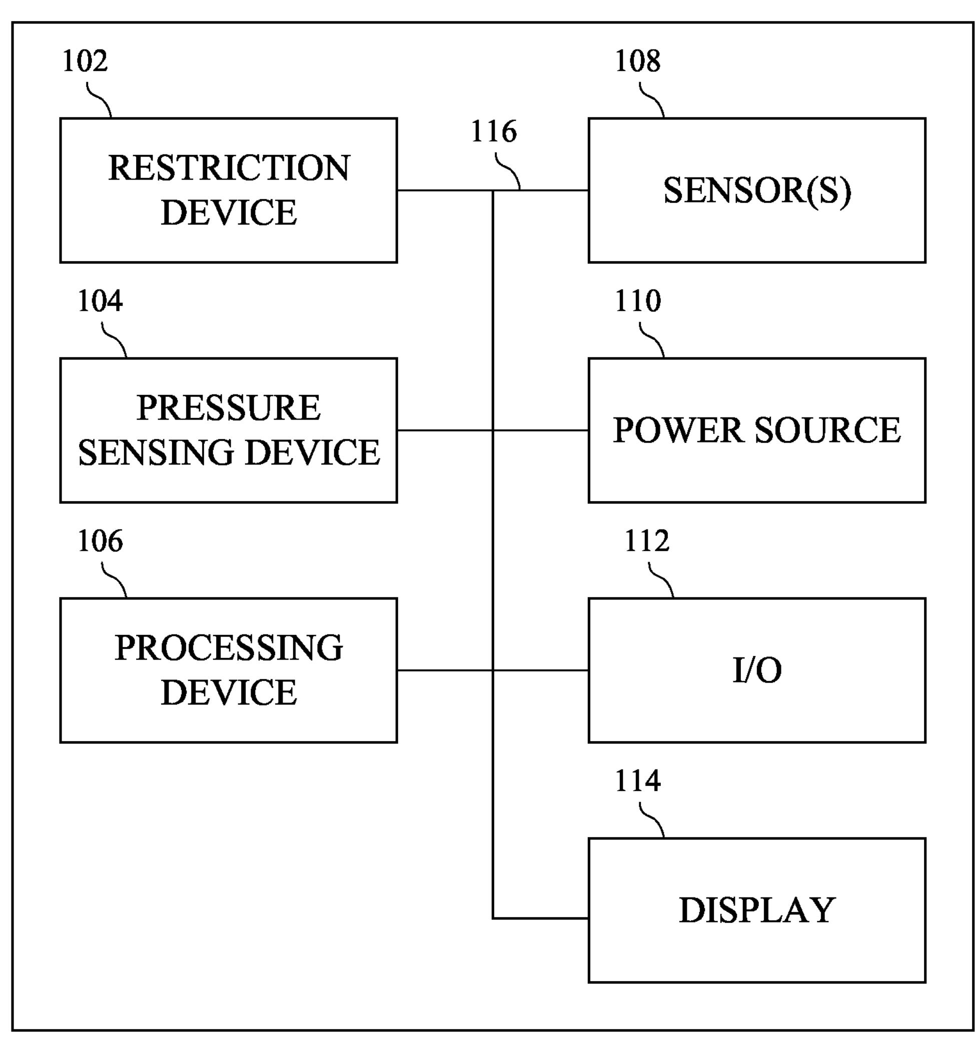
FIG. 1A shows a block diagram of an example blood pressure management system.

It should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

Embodiments disclosed herein are directed to blood pressure measurement systems for determining one or more blood pressure parameters of a user. Examples of blood pressure parameters can include systolic blood pressure, diastolic blood pressure, mean pressure, blood pressure variability, or other physiological parameters for a user. The system can include a restriction device that is configured to apply an external pressure cycle to a user to cause restriction of blood flow through one or more blood vessels of the user. In some cases, the external pressure cycle may be referred to as an applied pressure sweep. The restriction device can be an inflatable cuff, a band that tightens around the limb of a user, or any other suitable device. The system can also include a pressure sensing device that is configured to detect pressure changes within one or more blood vessels while the external pressure cycle is applied. For example, the pressure changes can be changes to the wave shape of pulse pressure occurring within a user's blood vessel as a result of the external pressure cycle. The system can analyze the detected pressures from the pressure sensing device to determine the one or more blood pressure parameters for the user. The non-invasive blood pressure measurement system and analysis techniques described herein may more accurately and repeatably determine one or more blood pressure parameters of a user.

Typical non-invasive blood pressure measurement techniques include auscultatory techniques, which are typically performed by a trained professional using an inflatable pressure cuff and stethoscope to listen for sounds that are characteristic of changes in blood flow through a person's vessels. The need for a trained professional can make it difficult for a user to perform routine blood pressure measurements, and the results can be variable due to differences between different professionals. Automated auscultatory machines also tend to be less accurate than desired. For example, automated auscultatory machines can pick up sound artifacts due to movement of a user and/or be less accurate due to trouble sensing physiological variations of the Korotkoff sounds patterns associated with different users. Automated oscillometer devices also tend to be less accurate and/or have greater variability in determining systolic and/or diastolic pressures.

The blood pressure measurement system described includes devices and analysis techniques that may result in more accurate and/or more repeatable non-invasive blood pressure measurements for a user. The system can include using a pressure sensing device that detects pressures within a user's blood vessel while an external pressure cycle is applied to the user to induces changes in flow through the user's blood vessel. In some cases, the pressure sensing device can be configured to detect pressures for the pulse pressure waves that occur within the user's blood vessel and output a signal indicative of the detected pressures for the pulse pressure waves. In this regard, the output pressures include data that corresponds to changes in the blood pressure that occurs during each pulse pressure wave. The output detected pressures can include information related to a minimum pulse pressure, maximum pulse pressure, rates of pressure change, changes in pressure due to valve closure, pulse frequency, and/or other pulse pressure events.

In some embodiments, the detected pressures can be output in a signal and received by a processing device and analyzed to determine blood pressure parameters for the user. The analysis can include determining a set of pressure measurements from the signal and identifying characteristic features in each pulse pressure wave measurement that was taken during the external pressure cycle. For example, the processing device can identify a minimum pressure value for each pulse pressure wave, which may correspond to a transition between systole and diastole and/or vice versa. The processing device can also be configured to determine a data value corresponding to an uptick pressure that occurs in the descending pressure phase of each pulse pressure wave. In some cases, the uptick pressure corresponds to a dicrotic notch, which can be a result of aortic valve closure and/or other pressure event that occurs during a user's cardiac cycle. The uptick pressure can be maximum uptick pressure for the upstroke phase (e.g., dicrotic notch portion) of each pressure wave. The processing device can be further configured to determine a first fit parameter, such as a first trend line, based on the determined minimum pressure value for each pulse pressure wave, and a second fit parameter, such as a second trend line, based on the determined uptick pressure for each pulse pressure wave. The processing device can determine an intersection of the first fit parameter with the second fit parameter. This intersection may occur while the external pressure cycle is applied to the user. The intersection may be used to identify a pulse pressure wave that is used to determine one or more blood pressure parameters of a user. For example, a maximum pressure value from a pulse pressure wave corresponding to the intersection of the first and second fit parameters can be used to determine a systolic blood pressure of a user. In this regard, the combination of obtaining pulse pressure data while an external pressure cycle is applied and using a processing device to identify specific pressure events occurring over the set of pulse pressure waves may provide a more accurate and/or repeatable system for determining blood pressure parameter(s) of a user.

These and other embodiments are discussed below with reference to FIGS. 1-6. However, those skilled in the art will readily appreciate that the detailed description given herein with respect to these Figures is for explanatory purposes only and should not be construed as limiting.

FIG. 1A shows a block diagram of an example blood pressure measurement system 100. The blood pressure measurement system 100 can include a restriction device 102, a pressure sensing device 104, a processing device 106, one or more other sensor(s) 108, a power source 110, an input-output (I/O) mechanism 112, and a display 114. As described herein the blood pressure measurements system 100 can be operated to determine a blood pressure of a user.

The restriction device 102 can be configured to apply an external pressure cycle to one or more blood vessels of a user. In some cases, the restriction device 102 can be an inflatable cuff that wraps around the limb of a user. The cuff can be inflated to compress the limb, thereby compressing blood vessels within the limb. In other embodiments, the restriction device 102 can be a band that is configured to progressively tighten or otherwise increase a force applied to the limb of the user. In other examples, the restriction device 102 can be any device that can apply increasing pressure to a skin surface of a user to compress an underlying blood vessel. In this regard, the restriction device 102 may not wrap around the limb of the user.

The restriction device 102 can be configured to control how the pressure is applied to a user. For example, the restriction device 102 can control a rate of pressure increase and/or decrease, hold a specific pressure for a defined period, and so on. In further embodiments, the restriction device 102 can be controlled based on one or more measured parameters such as outputs from the pressure sensing device 104 and/or other sensors 108. In some cases, the restriction device 102 can be integrated with or be part of another device, such as a band on a smartwatch, a band that interface with a smart device such as a smartphone, tablet, computer or other electronic device. The restriction device 102 may communicate with one or more other devices using wireless and/or wired connections.

The pressure sensing device 104 can be configured to detect pressures within one or more blood vessels of a user. In some embodiments the pressure sensing device 104 is configured to measure pressures in the blood vessel(s) while the restriction device 102 is performing an external pressure cycle on the user. The pressure sensing device 104 can output one or more signals that are indicative of the detected pressures. In some embodiments, the pressure sensing device 104 can include multiple pressure sensing units that can be positioned at different locations on a user and each configured to output one or more pressure signals. In this regard, the pressure sensing device 104 can output pressure signals corresponding to the different locations on the user. The location and pressure data may be correlated such that each location is identified and associated with corresponding pressure measurements. For example, a first pressure sensing unit can be located on the upper arm of a user and a second pressure sensing unit can be located on a lower arm such as the wrist of the user. In these embodiments, the pressure sensing device 104 can output pressure signals, which are associated with their location on either the upper arm or lower arm.

In further examples, the pressure sensing device 104 can include multiple pressure sensing units located around a user's limb, such as a wrist of the user. Outputs from these pressures sensing units may be used to determine a blood pressure parameter of a user. In some cases, the pressure signals from multiple pressure sensing units may be compared to determine a subset of one or more pressure sensing units that are used to determine a blood pressure parameter. For example, pressure sensing units with the greater magnitude inputs from the user, may be oriented closer to a major blood vessel. Accordingly, the blood pressure measurement system 100 may use these stronger inputs from a subset of one or more pressure sensing units to determine a blood pressure parameter of a user. In other examples, outputs from different pressure sensing units can be compared to determine an orientation of the pressure sensing device 104 with respect to anatomical features of a user. For example, if the pressure sensing device 104 is located on a user's wrist, pressure sensing units that detect weaker pressure inputs can be determined to be located on a back side of the wrist and positioned over one or more bone such as the radius or ulna. Pressure sensing units that detect stronger pressure inputs can be determined to be located on the front side of the writs and positioned over one or more major blood vessels such as the radial and ulnar arteries. In some cases, the pressure sensing device 104 can include an array of pressure sensing units, and the outputs of each of these units can be analyzed to determine a pressure map across the skin surface of the user, which can be used to determine a more accurate position of the pressure sensing units with respect to the user's anatomy. In some cases, the pressure sensing device 104 can be operated in response to determining its position with respect to a user. For example, pressure sensing units can be activated, deactivated, filtered, or their function modified based on their relative location to one or more anatomical features such as a specific blood vessel.

The pressure sensing device 104 can be devices that are capable of measuring blood pressure of a user. In some cases, the pressure sensing device 104 can measure the pulse pressure of a user using an applanation tonometer. For example, the pressure sensing device 104 can include one or more applanation pressure transducers that contact the user to measure a pulse pressure within one or more blood vessels of the user. The applanation pressure transducers can be operated to measure changes in pressure that occur in a user's blood vessel during a cardiac cycle (e.g., a pulse pressure wave). That is, the pressure sensing device 104 can detect pulse pressure changes that occur due to systole and diastole cardiac phases. In this regard, the pressure sensing device 104 can be configured to output signal(s) indicative of pressure changes that occur over a single cardiac cycle. Additionally, the pressure sensing device can measure pressure changes for multiple pulse cycles, and thus, output signal(s) indicative of pulse pressure waves that occur over multiple cardiac cycles. Additionally or alternatively, the pressure sensing device 104 can include other types of pressure sensing units. For example, the pressure sensing device can include piezoelectric sensors, oscillometric sensors, auscultatory sensors, force transducers, strain gauges, capacitive sensors, or any other suitable pressure sensor.

The processing device 106 can control some or all of the operations of the blood pressure measurement system 100. The processing device 106 can communicate, either directly or indirectly, with some or all of the components of the blood pressure measurement system 100. For example, a system bus or other communication mechanism 116 can provide communication between the processing device 106, the restriction device 102, the pressure sensing device 104, the sensors 108, the power source 110, the input/output (I/O) mechanism 112, memory, one or more displays 114, or other components of the blood pressure measurement system.

The processing device 106 can be implemented as any electronic device capable of processing, receiving, or transmitting data or instructions. For example, the processing device 106 can be a microprocessor, a central processing unit (CPU), an application-specific integrated circuit (ASIC), a digital signal processor (DSP), or combinations of such devices. As described herein, the term "processing device" is meant to encompass a single processor or processing unit, multiple processors, multiple processing units, or other suitable computing element or elements.

It should be noted that the components of the blood pressure measurement system 100 can be controlled by multiple processors. For example, select components of the blood pressure measurement system 100 (e.g., a sensor(s) 108) may be controlled by a first processor and other components of the blood pressure measurement system 100 (e.g., the I/O mechanism 112) may be controlled by a second processor, where the first and second processors may or may not be in communication with each other.

The processing device 106 can be configured to receive and/or transmit one or more pressure signals from the pressure sensing device 104. In some cases, the received signals can include signals indicative of pulse pressure measurements from the pressure sensing device 104. Transmitted signals can include control signals, which can be used to initiate and/or terminate a measurement sequence, signals that modify operating parameters of the pressure sensing device 104 such as a sample rate, other controllable parameters, and so on.

The processing device 106 can be configured to analyze the received pressure signals to determine one or more blood pressure parameters of a user as described herein. For example, the processing device 106 can use the received pressure signal(s) to determine a set of pressure measurements for a set of pulse pressure waves that occur within the blood vessel while the external pressure cycle is applied to a user. These pressure measurements may be further processed by the processing device to determine a blood pressure of a user as described herein, for example with relation to FIGS. 2-6.

The blood pressure measurement system 100 may also include one or more sensor(s) 108 positioned almost anywhere on the blood pressure measurement system 100. The sensor(s) 108 can be configured to sense one or more type of parameters, such as but not limited to, pressure, sound, light, touch, heat, movement, relative motion, biometric data (e.g., biological parameters), and so on. For example, the sensor(s) 108 may include a pressure sensor, an auditory sensor, a heat sensor, a position sensor, a light or optical sensor, an accelerometer, a pressure transducer, a gyroscope, a magnetometer, a health monitoring sensor, and so on. Additionally, the one or more sensor(s) 108 can utilize any suitable sensing technology, including, but not limited to, capacitive, ultrasonic, resistive, optical, ultrasound, piezoelectric, and thermal sensing technology.

The power source 110 can be implemented with any device capable of providing energy to the blood pressure measurement system 100. For example, the power source 110 may be one or more batteries or rechargeable batteries. Additionally or alternatively, the power source 110 can be a power connector or power cord that connects the blood pressure measurement system 100 to another power source, such as a wall outlet.

The I/O mechanism 112 can transmit and/or receive data from a user or another electronic device. An I/O mechanism 112 can include a display, a touch sensing input surface, one or more buttons (e.g., a graphical user interface "home" button), one or more cameras, one or more microphones or speakers, one or more ports, such as a microphone port, and/or a keyboard. Additionally or alternatively, an I/O device or port can transmit electronic signals via a communications network, such as a wireless and/or wired network connection. Examples of wireless and wired network connections include, but are not limited to, cellular, Wi-Fi, Bluetooth, IR, and Ethernet connections.

The blood pressure measurement system 100 may also include a display 114. The display 114 may include a liquid-crystal display (LCD), organic light-emitting diode (OLED) display, light-emitting diode (LED) display, or the like. If the display 114 is an LCD, the display 114 may also include a backlight component that can be controlled to provide variable levels of display brightness. If the display 114 is an OLED or LED type display, the brightness of the display 114 may be controlled by modifying the electrical signals that are provided to display elements. The display 114 may correspond to any of the displays shown or described herein The blood pressure measurement system 100 is generally illustrated as being contained within a housing. In some embodiments, the blood pressure measurement system 100 may be an integrated device such as a smartwatch, an arm-worn device that includes a single housing containing components such as the processing device 106, the sensor(s) 108, power source 110, I/O mechanism 112, and display 114, and coupled with the restriction device 102 and/or pressure sensing device 104, or other integrated wearable device. In other embodiments, the blood pressure measurement system 100 can include multiple discrete/separate components that are communicably connected (wired or wirelessly) to exchange data and control operation of the system. For example, the blood pressure measurement system 100 can include a first wearable device that includes the restriction device 102 and the pressure sensing device 104 that communicates data to/from a second device such as a smartphone, tablet, computer or any other suitable electronic device. In some cases, the restriction device 102 and the pressure sensing device 104 can be separate devices that are worn by a user, for example at different locations on their body. In some cases, the blood pressure measurement system 100 can include multiple restriction devices 102 and/or multiple pressure sensing devices 104, which can be positioned at different locations on a user and operated in coordination to determine one or more blood pressure parameters of a user.

Figure 1B:
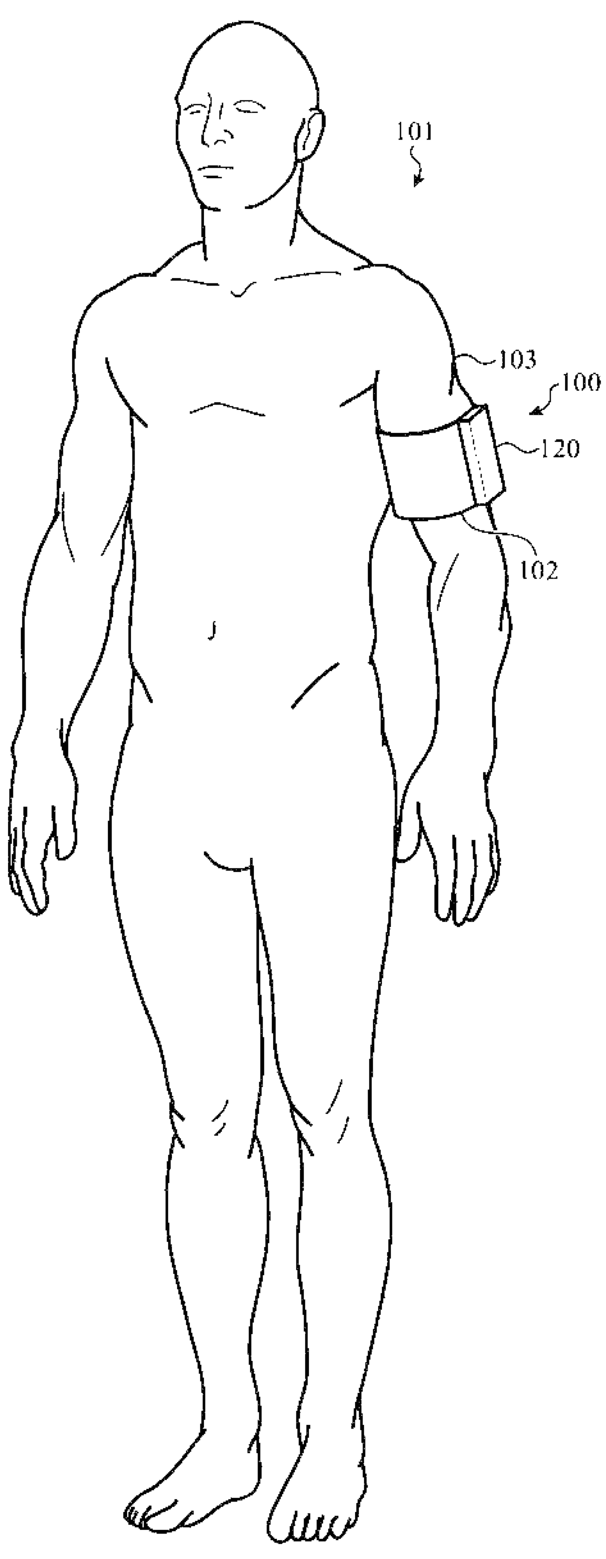
FIG. 1B shows an example blood pressure measurement system worn by a user.

FIG. 1B shows an example of the blood pressure measurement system 100 being worn by a user 101. In the example shown in FIG. 1B, the restriction device 102 can be a cuff, such as an inflatable cuff, that wraps around a limb 103 of the user 101, and a housing 120 that can include one or more components of the system such as the pressure sensing device 104, the processing device 106, the one or more sensors 108, the power source 110, the I/O mechanism 112, and the display 114 described herein. In some cases, the blood pressure measurement system 100 can include multiple devices that are communicably coupled, and exchange data to perform different aspects of the techniques described herein. For example, a first device can include the restriction device 102, such as an inflatable cuff, the pressure sensing device 104 and an I/O mechanism 112. A second device can be another electronic device that receives the detected blood pressure data from the first device and processes the data to determine a blood pressure parameter of a user. Examples of the second device include a smartwatch, a smartphone, a tablet computing device, a computer, or other suitable devices. In some cases, the blood pressure measurement system 100 can be implemented as a wearable device such as a smartwatch, and the restriction device 102 can be incorporated into the smartwatch. For example, the restriction device 102 can be integrated into a strap of the smartwatch.

Figure 1C:
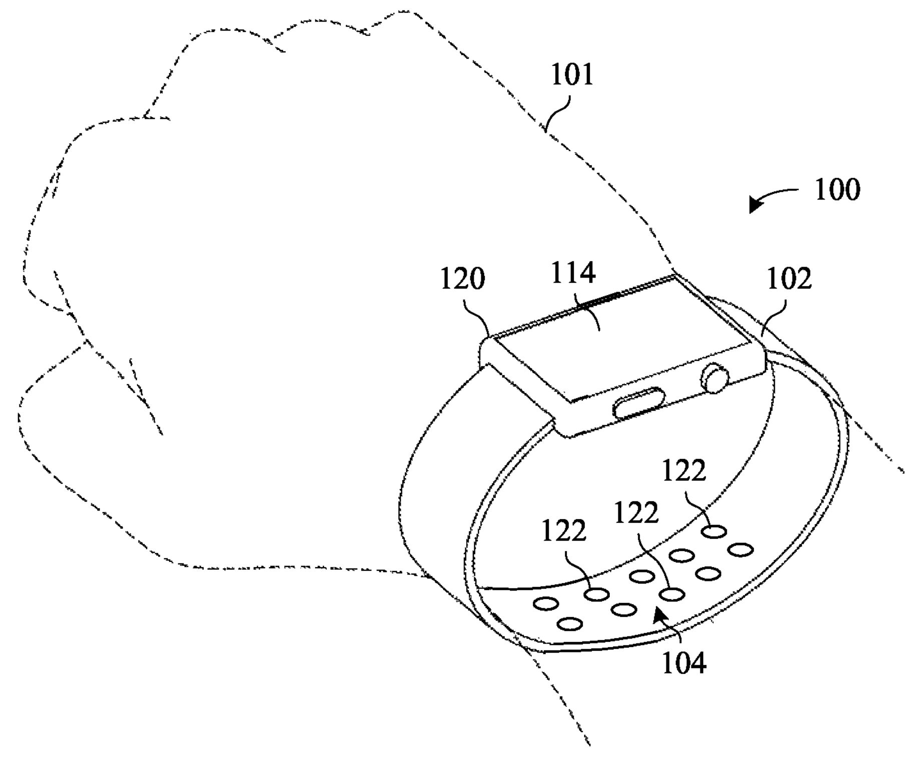
FIG. 1C shows an example blood pressure measurement system worn by a user.

FIG. 1C shows an example of the blood pressure measurement system 100 that can be worn around a wrist or other portion of a user 101. In the illustrated example, the housing 120 can be coupled to a restriction device 102 that includes a band that wraps around a limb of a user 101. The pressure sensing device 104 can include an array of pressure sensing units 122 (three of which are labeled for clarity). The array of pressure sensing units 122 can include a variety of configurations. For example, the array of pressure sensing units 122 can have different numbers of pressure sensing units 122 and different layouts, such as rectangular, circular, or any other suitable layout. In some cases, the array of pressure sensing units 122 can extend around a circumference of a limb of the user 101. The array of pressure sensing units 122 can be positioned on an inside surface of the band such that they contact the user 101 when the blood pressure measurement system 100 is being worn. The pressure sensing units 122 can include different types of sensors such as those described herein. For example, the array of pressure sensing units 122 can include tonometers, piezoelectric sensors, capacitive sensors, force transducers, fluid pressure transducer, strain gauges, or any other suitable pressure sensing device.

The restriction device 102 can also be implemented in a variety of ways. In some cases, the restriction device 102 can be a band that tightens around a wrist or other part of the user 101 to apply an external pressure cycle to the user 101. For example, the band can be an inflatable cuff that expands to apply an external pressure cycle to the user 101. In some cases, the restriction device 102 can include one or more actuators positioned beneath the array of pressure sensing units 122. The actuator(s) can apply a localized external pressure cycle to the user 101 in the area of the one or more of the pressure sensing units 122. For example, the actuator(s) can be configured to press one or more of the pressure sensing units 122 against a skin surface of the user 101.

The housing 120 can include a display 114 and contain one or more components of the blood pressure measurement system 100 such as the processing device 106, the one or more sensors 108, the power source 110 and the I/O mechanism 112 and described herein.

Figure 2:
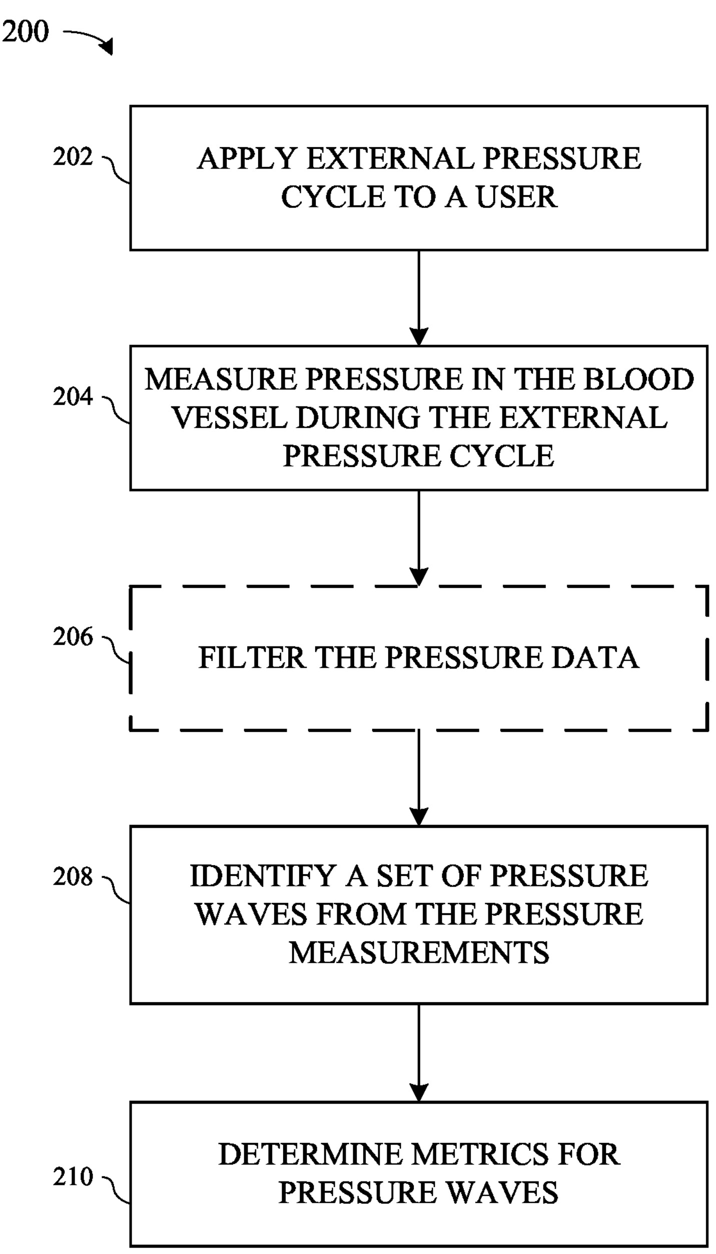
FIG. 2 is a flowchart of an example process for operating a blood pressure measurement system.

FIG. 2 is a flowchart of an example process 200 for operating a blood pressure measurement system, such as the blood pressure measurement system 100 described herein.

At 202, the process 200 can include applying an external pressure cycle to a user to compress one or more blood vessels. Applying the external pressure cycle can include inflating a cuff or otherwise compressing a limb or other body part of a user. In other cases, the external pressure cycle can include deflating a cuff or otherwise decompressing a limb or other body part of a user. In some cases, the external pressure cycle can include both compression and decompression phases. In some cases, the rate of the pressure cycle can be controlled such that a compression and/or decompression of the user's skin/blood vessels occurs in a defined manner. For example, a restriction device to compress and/or decompress a user's skin/blood vessels at a constant rate. In some cases, the compression and decompression phases can be performed at the same rate. In other cases, the compression and decompression phases can be performed at different rates and/or have differing profiles. For example, at 202 the process can include a hold at a specific pressure for a defined amount of time or in response to an event. In some cases, the rate and or compression/decompression profiles can be adjusted using outputs from one or more sensors. For example, the rate of compression and/or decompression can be decreased to increase the amount of pressure measurement obtained during an external compression cycle, which may improve the accuracy and/or repeatability of determining blood pressure parameters.

In some embodiments the external pressure cycle can be applied in increasing or decreasing steps that include holding at one or more incremental pressure values for a period of time. In other cases, the pressure may be increased or decreased in different ways, such as by changing an inflation and/or deflation rates at different portions of the external pressure cycle.

At 204, the process 200 can include detecting the pressure in a blood vessel of a user during the external pressure cycle. In some cases, this can include initiating a measurement sequence at the pressure sensing device to measure pressures while the restriction device compresses and/or decompresses a portion of a user's body. The measurement sequence can begin before the external pressure cycle starts to obtain baseline data for a user and continue until the external pressure cycle is complete. In some cases, the measurement sequence can occur until the system has determined a blood pressure parameter for a user. For example, the system may determine a blood pressure parameter for a user, after a pressure ramp phase. Accordingly, at step 204, the system can end the measurement sequence and/or the external pressure cycle without performing both a compression and decompression phases. In other cases, multiple external pressure cycles can be applied to a user and the pressure in the blood vessel can be monitored over the multiple external pressure cycles, which may be combined or otherwise analyzed to determine a blood pressure parameter, accuracy, confidence determination or other metrics associated with the pressure measurements. The pressure sensing device can output a signal indicative of the detected pressures to a processing device, which can determine a set of pressure measurements for the detected pressures.

At 206, the process 200 can include filtering and/or normalizing the measured pressure data. This step may be part of the process for determining a blood pressure parameter of a user. For example, the blood pressure measurement data can be normalized to account for the pressure applied by the external pressure ramp. In this regard, the normalized pressures can primarily include data related to changes in blood pressure over a pulse pressure wave while increases and/or decreases in the blood pressure due to the external pressure ramp are minimized or removed. In some cases, filtering the pressure data can include applying one or more of a low pass filter, high pass filter, band pass filter, data transformations such as a Fourier transformation, or other suitable signal processing techniques. In other cases, normalizing and/or filtering the pressure data can include adjusting the pressure data based on the pressure applied during the external pressure ramp. For example, the applied pressure can be measured and used to normalize and/or filter the pressure data.

At 208, the process 200 can include identifying a set of pressure waves from the set of pressure measurements. This can include analyzing and/or performing signal processing techniques to identify individual pressure waves corresponding to a cardiac cycle of a user (systole and diastole). In some cases, this can include identifying valleys and peaks in the pressure data and determining transition regions or points between two or more subsequent cardiac cycles. In some cases, identifying pressure waves can include identifying a portion of the pressure wave corresponding to systole, which can include an ascending or increasing pressure phase. Identifying the pressure waves can also include identifying a portion of the pressure wave corresponding to diastole, which can include a descending pressure phase.

At 210, the process 200 can include determining one or more pressure metrics for pressure waves in the set of pressure waves. This can include analyzing the pressure data to identify a minimum pressure value and/or maximum pressure value for one or more pulse pressure waves. In some cases, determining one or more pressure metrics can include identifying pressure changes in the pressure measurement data to correspond to cardiac events such as valve closure. For example, the pressure measurement data can be analyzed to determine a pressure uptick that corresponds to a localized increase in pressure, which can result from valve closure. Such pressure events may be referred to as a dicrotic notch. In some cases, step 210 can include determining a pressure value corresponding to the dicrotic notch, such as a localized maximum uptick pressure of the pressure upstroke. In some cases, step 210 can include identifying a dicrotic event in the pressure measurement data during a descending pressure phase of an identified pulse pressure wave. Step 210 can include analyzing the pressure measurement data to determine other pressure events such as localized pressure changes corresponding to pressure reflection events, variations due to compliance of blood vessels, or other anatomical effects of a user. In some cases, step 210 may include identifying arrythmias, valve defects, or other cardiac abnormalities.

Figure 3:
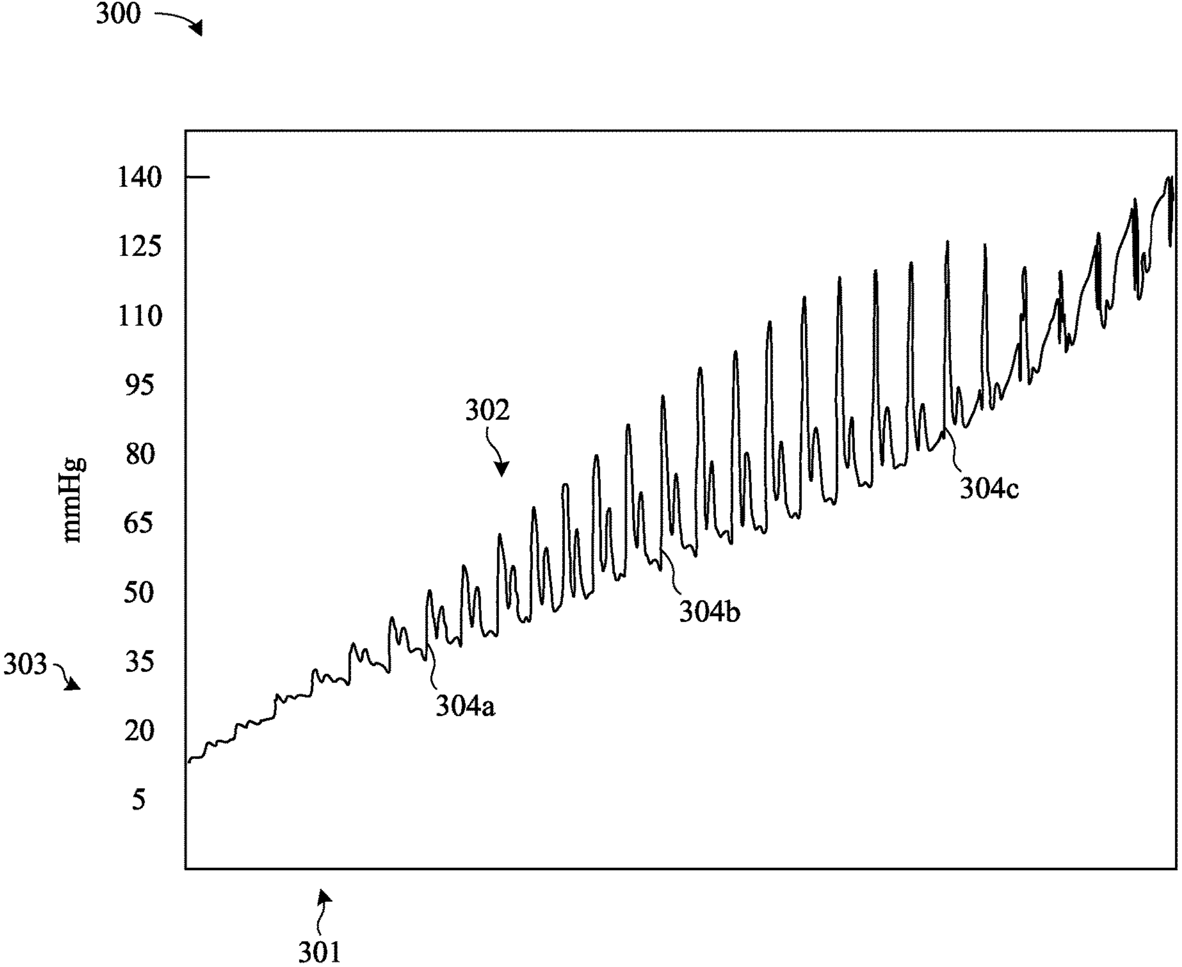
FIG. 3 shows an example set of blood pressure measurement obtained during operation of the blood pressure measurement system.

FIG. 3 shows an example set of detected blood pressures 300 obtained during operation of the blood pressure measurement systems described herein such as blood pressure measurement system 100. The set of blood pressure measurements 300 show an example of measurements taken while an external pressure sensor is being applied to a blood vessel of a user. The detected blood pressures 300 is shown in graph form for the sake of illustration, although it will be appreciated that this data may be stored in computer readable form, such as a set of values. The graph showing the detected blood pressures 300 can include a first axis 301 corresponding to time and a second axis 303 corresponding to pressure, which is shown in millimeters of mercury (mmHg) in this example. The pressure data 302 includes pressure measurements obtained during an external pressure cycle, such as compression of a user's blood vessel by tightening a cuff around a limb of a user. As shown, the pressure data 302 can include a set of pulse pressure waves 304, three of which are labeled for clarity. The amplitude of each pulse pressure wave 304 may increase as the restriction device increases an external pressure on the user. For example, the example shown in FIG. 3 includes increasing the external pressure over time. The first pulse pressure wave 304*a* corresponds to a lower external pressure on the user, the second pulse pressure wave 304*b* corresponds to an increased external pressure on the user and the third pulse pressure wave 304*c* corresponds to further increased pressure on the user. As shown the external pressure can result in an increase of the average pressure for each pulse pressure wave 304. In some cases, a set of blood pressure measurements 300 can be normalized and/or filtered to remove the effects of the increasing external pressure. In some cases, this results in the set of blood pressure measurements including data that shows the pressure variations within each pressure cycle on a common scale (e.g., without the effects of the increasing external pressure).

Figure 4:
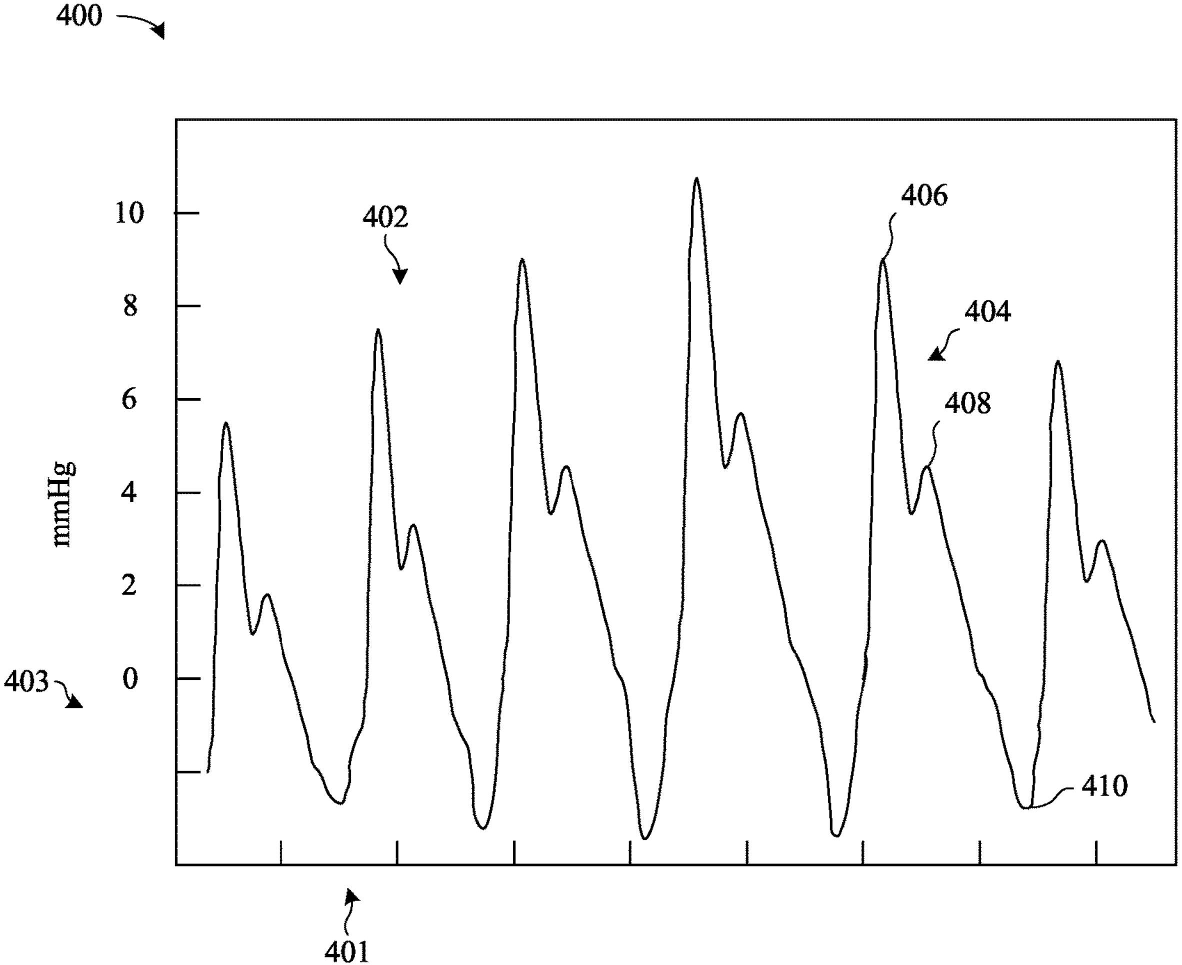
FIG. 4 shows an example set of processed blood pressure measurements.

FIG. 4 shows an example set of pressure measurements 400, which have been processed to generate normalized pressure data including pressure changes for each pulse pressure cycle (e.g., with external pressure removed). The pressure measurements 400 can be an example of the resulting pressure data from normalizing the detected blood pressures 300 shown in FIG. 3. For the sake of illustration, the set of pressure measurements 400 can display blood pressure data 402 in graph form, and the blood pressure data 402 can be stored and/or processed in computer readable formats. The set of pressure measurements 400 show the blood pressure data 402 with respect to a graph having a first axis 401 representing time and a second axis 403 representing pressure shown in mmHg.

The blood pressure data 402 can include a set of pulse pressure waves 404, one of which is labeled for clarity. One or more of the pulse pressure waves 404 can be analyzed as described herein, such as in reference to FIG. 2, to determine metrics such as a maximum pressure 406, a pressure upstroke 408 and a minimum pressure 410. For example, the maximum pressure 406 can be a localized maximum pressure value for the pulse pressure wave 404, and the minimum pressure 410 can be a localized minimum pressure value for the pulse pressure wave 404. In some cases, the pressure upstroke 408 may be determined for a descending pressure phase of the pulse pressure wave 404, which can occur between the maximum pressure 406 and the minimum pressure 410. In some examples, the pressure upstroke 408 can be identified as a maximum uptick pressure that occurs in the descending pressure phase and may correspond to one or more cardiac events such as aortic valve closure and/or reflected pulse pressure waves.

Figure 5:
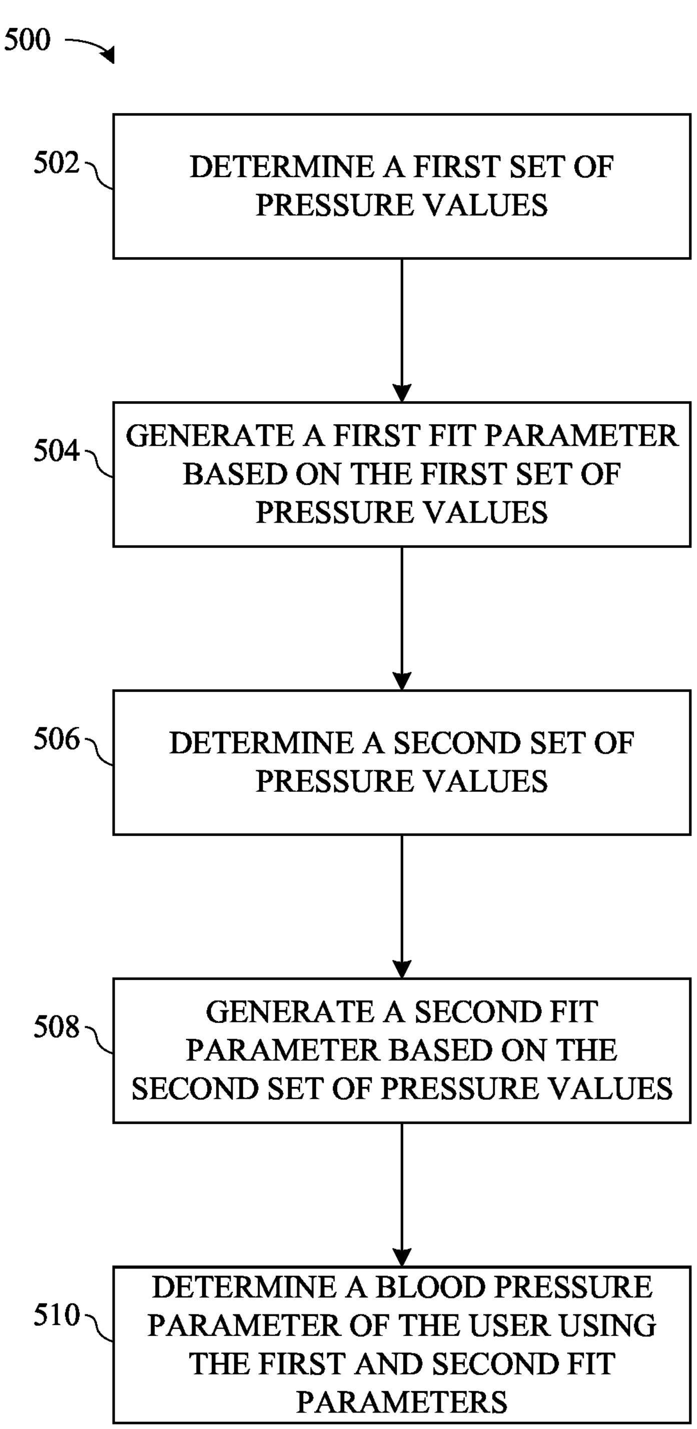
FIG. 5 is a flowchart showing example operation of determining a blood pressure parameter from blood pressure measurements.

FIG. 5 is a flowchart showing example process 500 for determining a blood pressure parameter from blood pressure measurements. The process 500 can be performed by the blood pressure measurement system described herein (e.g., blood pressure measurement system 100) and be performed on analyzed blood pressure measurement data such as blood pressure measurements 300 and 400.

At 502, the process 500 can include determining a first set of pressure values from the set of pressure measurements. In some cases, the first set of pressure values includes pressure values that correspond to a minimum pressure for each pulse pressure wave in a set of measured pulse pressure waves. The set of measured pulse pressure waves can include pressure data that was obtained while the external pressure cycle was applied to the user, and the minimum pressure values include local minimum pressure for each pulse pressure wave as described herein.

At 504, the process 500 can include generating a first fit parameter based on a first set of pressure values. The first fit parameter can be a parameter such as a fit line that represent a numerical trend of the first set of pressure values over the data set. The first fit parameter can represent the trend of changes in pressure values corresponding to the minimum pressures that occur as the externally applied pressure is increased. In some cases, the first fit parameter represents a numerical trend for the set of minimum pressure values for each pulse pressure wave. In some cases, determining the first fit parameter can include performing a regression analysis on the first set of pressure values (e.g., minimum pressures for each pulse pressure wave). In some cases, generating a first fit parameter can include generating an extrapolated data set for the first set of pressure values. For example, the first fit parameter can be a trend line that defines one or more data points outside of the first set of pressure values.

At 506, the process 500 can include determining a second set of pressure values from the set of blood pressure measurements In some cases, the second set of pressure values includes pressure values that correspond to a pressure upstroke that occurs during a descending pressure phase of each pulse pressure wave, as described herein. For example, the pressure upstroke can correspond to a dicrotic notch that occurs as a result of aortic valve closure or due to other cardiac events such as reflected pressure waves. The set of measured pulse pressure waves can include pressure data that was obtained while the external pressure cycle was applied to the user.

At 508, the process 500 can include generating a second fit parameter based on a second set of pressure values. The second first parameter can be a parameter such as a fit line that represents a numerical trend of the second set of pressure values over the data set. The second fit parameter can represent the trend of changes in pressure values corresponding to the pressure upstrokes that occur as the externally applied pressure is increased and/or decreased. In some cases, the second fit parameter represents a numerical trend for the set of pressure values corresponding to a pressure upstroke that occurs during descending pressure phase for measured pulse pressure waves in the set of pulse pressure waves, as described herein. In some cases, determining the second fit parameter can include performing a regression analysis on the second set of pressure values (e.g., pressure upstroke for each pulse pressure wave). In some cases, generating a second fit parameter can include generating an extrapolated data set for the second set of pressure values. For example, the second fit parameter can be a trend line that defines one or more data points outside of the second set of pressure values.

At 510, the process 500 can include determining a blood pressure parameter of the user using the first and second fit parameters. Determining the blood pressure parameter can include determining an intersection of the first fit parameter and the second fit parameter, which may occur as the externally applied pressure is increased and/or decreased. The intersection of the first fit parameter and the second fit parameter can be used to identify a particular pressure wave in the set of pulse pressure waves, that will be used to determine the blood pressure parameter of a user. For example, the pulse pressure wave that corresponds to the intersection of the first fit parameter and the second fit parameter can be used to determine the blood pressure parameter. In some cases, the blood pressure parameter is a systolic pressure of the user, and the maximum value from the pressure wave corresponding to the intersection of the first and second fit parameters is used to determine the systolic blood pressure of the user.

Figure 6A:
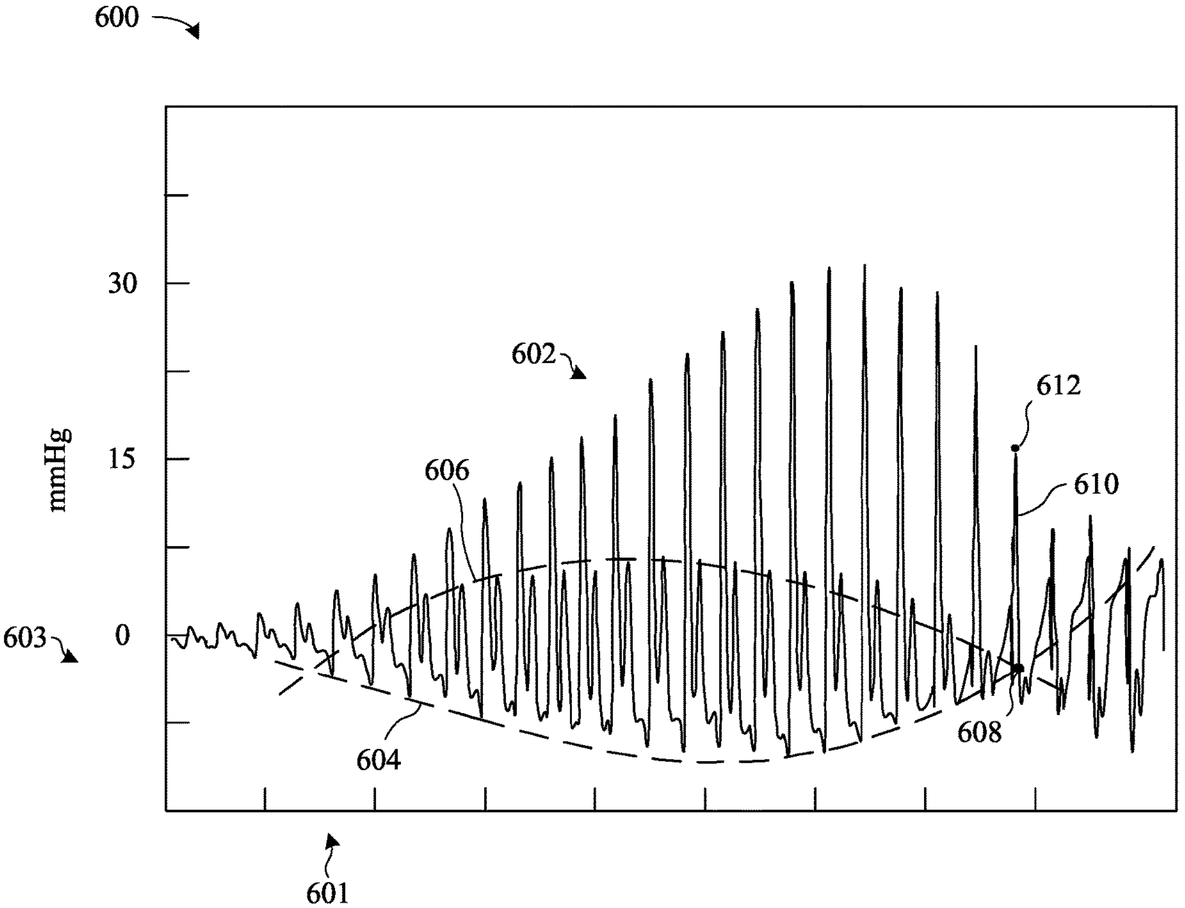
FIG. 6A shows an example set of blood pressure data that is used to determine a blood pressure parameter of a user.

FIG. 6A shows an example set of blood pressure data set 600 that is used to determine a blood pressure parameter of a user. The blood pressure data set 600 illustrated in FIG. 6A shows an example process using normalized pressure data as described herein. The blood pressure data set 600 can include a set of pressure data 602 that is used to generate a first fit parameter 604 and a second fit parameter 606. The set of pressure data 602 can include measured pulse pressure data as described herein that is displayed in graph form for the sake of illustration. Accordingly, it will be appreciated that as implemented, the pressure data 602 can be in computer readable form and processed using computer logic. The pressure data 602 is shown on a graph including a first axis 601 representing time and a second axis 603 representing pressure in mmHg.

As described herein the first fit parameter 604 can be based on a minimum pressure value for each pulse pressure wave and the second fit parameter 606 can be based on a pressure upstroke for each pulse pressure wave. An intersection point 608 of the first fit parameter 604 and the second fit parameter 606 can be determined. As described herein the pressure wave 610 can be identified as the pressure wave corresponding to the intersection point 608 of the first fit parameter 604 and the second fit parameter 606. In some cases, determining the corresponding pressure wave 610 can include determining a pressure wave that overlaps or partially overlaps with the intersection point 608. In other cases, determining the corresponding pressure wave 610 can include determining a pressure wave that occurs before or after the intersection point 608. For example, the system can be configured to select the corresponding pressure wave 610 as the first full pressure wave that occurs after the intersection point 608. In other cases, the system can be configured to select the corresponding pressure wave 610 as the first full pressure wave that occurs before the intersection point 608.

The corresponding pressure wave 610 can be used to determine a blood pressure parameter of a user. For example, the corresponding pressure wave 610 can be used to determine a systolic pressure of a user. In some cases, normalizing and/or filtering the blood pressure data to generate the blood pressure data set 600 can result in the pressure values being modified. Accordingly, once the pressure wave 610 is identified a maximum value 612 of the pressure wave 610 may be scaled or adjusted to account for any normalization and/or filtering. In some cases, this can include scaling the maximum pressure value 612 based on the normalization techniques. Additional or alternatively, this can include using the pressure wave 610 to identify the corresponding pressure wave in the un-normalized data set, and using the pressure values from the corresponding pressure wave in the un-normalized data set to determine the blood pressure parameter of a user. In some cases, a maximum pressure value from the corresponding wave in the un-normalized data set can be used to determine a systolic blood pressure of a user. In this regard, the blood pressure measurement system can be configured to perform one or more processes that more accurately determine a systolic blood pressure of user.

Figure 6B:
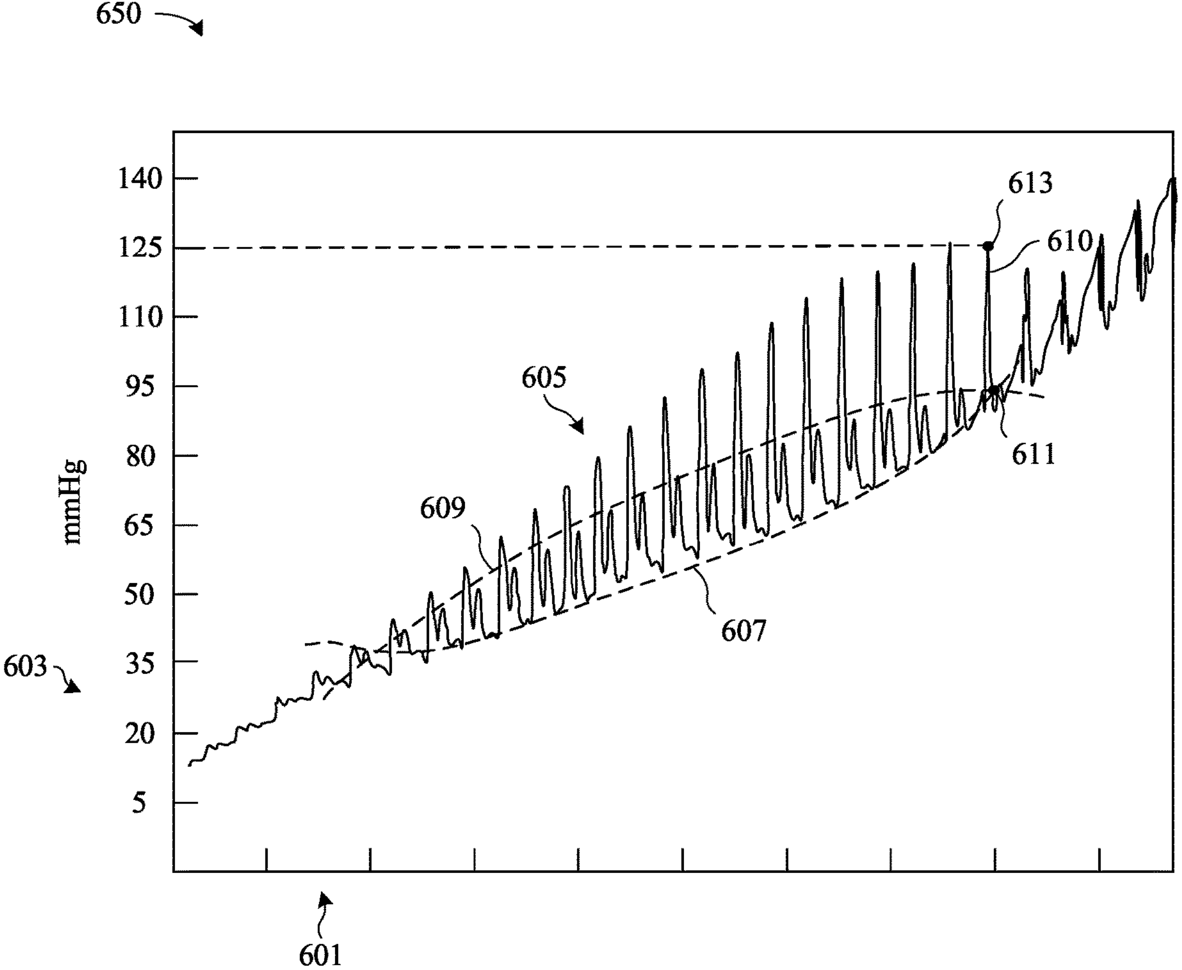
FIG. 6B shows an example set of blood pressure data that is used to determine a blood pressure parameter of a user.

FIG. 6B shows an example blood pressure data set 650 that is used to determine a blood pressure parameter of a user. The blood pressure data set 650 illustrated in FIG. 6B shows an example process using pressure data that has not been normalized to account for an applied external pressure cycle. In these cases, the blood pressure analyses can be performed directly on data sets the include the effects of the applied external pressure cycle.

The blood pressure data set 650 can include a set of pressure data 605 that is used to generate a first fit parameter 607 and a second fit parameter 609. The set of pressure data 605 can include measured pulse pressure data as described herein that is displayed in graph form for the sake of illustration. Accordingly, it will be appreciated that as implemented, the pressure data 605 can be in computer readable form and processed using computer logic. The pressure data 605 is shown on a graph including a first axis 601 representing time and a second axis 603 representing pressure in mmHg.

As described herein, the first fit parameter 607 can be based on a minimum pressure value for each pulse pressure wave and the second fit parameter 609 can be based on a pressure upstroke for each pulse pressure wave. An intersection point 611 of the first fit parameter 607 and the second fit parameter 609 can be determined. As described herein, the pressure wave 610 can be identified as the pressure wave corresponding to the intersection point 611 of the first fit parameter 607 and the second fit parameter 609. In some cases, determining the corresponding pressure wave 610 can include determining a pressure wave that overlaps or partially overlaps with the intersection point 611. In other cases, determining the corresponding pressure wave 610 can include determining a pressure wave that occurs before or after the intersection point 611. For example, the system can be configured to select the corresponding pressure wave 610 as the first full pressure wave that occurs after the intersection point 611. In other cases, the system can be configured to select the corresponding pressure wave 610 as the first full pressure wave that occurs before the intersection point 611.

The corresponding pressure wave 610 can be used to determine a blood pressure parameter of a user. For example, the corresponding pressure wave 610 can be used to determine a systolic pressure of a user. In some cases the systolic pressure can be determined to be a maximum value

613 of the pressure wave from the blood pressure data set 650. In this regard, the blood pressure analysis described herein may be performed on blood pressure data that has not been adjusted to account for the applied external pressure cycle. In some cases, the blood pressure data set 650 can be filtered or processed to modify the data for other factors, such as noise, outliers, and/or the like.

As described above, one aspect of the present technology is determining physiological parameters of a user such as blood pressure metrics, and the like. The present disclosure contemplates that in some instances this gathered data may include personal information data that uniquely identifies or can be used to contact or locate a specific person. Such personal information data can include demographic data, location-based data, telephone numbers, email addresses, Twitter IDs (or other social media aliases or handles), home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to provide haptic or audiovisual outputs that are tailored to the user. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining the privacy and security of personal information data. Such policies should be easily accessible by users and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and revised to adhere to applicable laws and standards, including jurisdiction-specific considerations. For instance, in the US, collection of or access to certain health data may be governed by federal and/or state laws, such as the Health Insurance Portability and Accountability Act ("HIPAA"); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of determining spatial parameters, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, haptic outputs may be provided based on non-personal information data or a bare minimum amount of personal information, such as events or states at the device associated with a user, other non-personal information, or publicly available information.

The foregoing description for purposes of explanation used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A system for determining blood pressure of a user comprising:

a restriction device configured to apply an external pressure cycle to a blood vessel of the user;

a pressure sensing device configured to:

detect pressures within the blood vessel during the external pressure cycle; and output a signal indicative of the detected pressures; and a processing device configured to:

receive the signal from the pressure sensing device;

determine a set of pressure measurements for a set of pulse pressure waves within the blood vessel during the external pressure cycle based on the signal;

determine a first set of pressure values, each pressure value in the first set of pressure values corresponding to a minimum pressure value for a respective pulse pressure wave in the set of pulse pressure waves;

determine a second set of pressure values, each pressure value in the second set of pressure values corresponding to a pressure upstroke that occurs during a descending pressure phase of the respective pulse pressure wave in the set of pulse pressure waves;

determine a first fit parameter defining a first fit line that represents changes in detected pressures of the first set of pressure values over the external pressure cycle;

determine a second fit parameter defining a second fit line that represents changes in detected pressures of the second set of pressure values over the external pressure cycle;

determine an intersection of the first fit line and the second fit line; and determine a blood pressure parameter of the user using the intersection of the first fit line and the second fit line.

2. The system of claim 1, wherein the processing device is configured to:

identify a pressure wave in the set of pulse pressure waves that corresponds to the intersection; and determine the blood pressure parameter using at least one pressure value corresponding to the pressure wave.

3. The system of claim 1, wherein the processing device is configured to associate the blood pressure parameter with a systolic blood pressure of the user.

4. The system of claim 1, wherein the restriction device comprises an inflatable cuff that is configured to wrap around a limb of the user.

5. The system of claim 1, wherein the pressure sensing device comprises an applanation tonometer that contacts the user during the external pressure cycle.

6. The system of claim 1, wherein the processing device is configured to:

determine a third set of pressure values, each pressure value in the third set of pressure values corresponding to a maximum pressure value for a respective pulse pressure wave in the set of pulse pressure waves; and identify the descending pressure phase of the respective pulse pressure wave as occurring between a respective minimum pressure value and a respective maximum pressure value.

7. The system of claim 1, wherein the processing device is configured to:

determine a maximum uptick pressure for the pressure upstroke; and associate each second pressure value in the second set of pressure values with the corresponding local maximum uptick pressure for the pressure upstroke.

8. A method for determining a blood pressure parameter of a user, the method comprising:

causing a restriction device to apply an external pressure cycle to a blood vessel of the user;

receiving a pressure signal corresponding to a set of measured pulse pressure waves occurring within the blood vessel during the external pressure cycle;

determining a first set of pressure values from the pressure signal, each pressure value in the first set of pressure values corresponding to a minimum pressure for a respective pulse pressure wave in the set of measured pulse pressure waves;

generating a first fit parameter defining a first fit line that represents changes in pulse pressure waves of the first set of pressure values over the external pressure cycle;

determining a second set of pressure values, each second pressure value in the second set of pressure values corresponding to a pressure upstroke that occurs during a descending pressure phase of the respective pulse pressure wave in the set of measured pulse pressure waves;

generating a second fit parameter defining a second fit line that represents changes in pulse pressure waves of the second set of pressure values over the external pressure cycle;

determining an intersection point of the first fit line and the second fit line;

using the intersection point to identify a corresponding pressure wave in the set of measured pulse pressure waves; and determining the blood pressure parameter of the user using the corresponding pressure wave.

9. The method of claim 8, wherein the blood pressure parameter is a systolic blood pressure.

10. The method of claim 8, wherein:

determining the first fit parameter comprises performing a first regression analysis on the first set of pressure values to generate a first extrapolated data set based on the first set of pressure values; and determining the second fit parameter comprises performing a second regression analysis on the second set of pressure values to generate a second extrapolated data set based on the second set of pressure values.

11. The method of claim 10, wherein determining the intersection point of the first fit parameter and the second fit parameter comprises determining an intersection between the first extrapolated data set and the second extrapolated data set.

12. The method of claim 8, wherein the blood pressure parameter of the user is based on a maximum value of the corresponding pressure wave.

13. The method of claim 8, further comprising:

generating a normalized set of pressure values; and determining the first set of pressure values and the second set of pressure values using the normalized set of pressure values.

14. The method of claim 8, wherein the descending pressure phase is determined by identifying a maximum pulse pressure and a minimum for pulse pressure for the respective pulse pressure wave.

15. The method of claim 8, wherein each second pressure value is based on a maximum of the pressure upstroke for the respective pulse pressure wave.

16. A blood pressure measurement device comprising:

a restriction device configured to wrap around a limb of a user and apply an external pressure cycle to a blood vessel of the user;

a pressure sensing device coupled to the restriction device and configured to:

detect pressures within the blood vessel during the external pressure cycle; and output a signal indicative of the detected pressures; and a processing device configured to:

receive the signal from the pressure sensing device;

analyze the signal to determine, for each pulse pressure wave occurring in the blood vessel during the external pressure cycle:

a local minimum pressure value that occurs between subsequent pulse pressure waves; and a descending pressure value that occurs during a descending phase of each pulse pressure wave; and determine a blood pressure parameter of the user based on the local minimum pressure value and the descending pressure value for each pulse pressure wave.

17. The blood pressure measurement device of claim 16, wherein the processing device is configured to:

generate a first fit parameter based on the local minimum pressure value for each pulse pressure wave;

generate a second fit parameter based on the descending pressure value for each pulse pressure wave; and determine the blood pressure parameter of the user based on an intersection of the first fit parameter and the second fit parameter.

18. The blood pressure measurement device of claim 16, wherein the descending pressure value corresponds to a pressure upstroke that occurs during the descending phase of each pulse pressure wave.

19. The blood pressure measurement device of claim 16, wherein the pressure sensing device comprises a tonometer that contacts the user during the external pressure cycle.

* * * * *